(12) United States Patent
Minato et al.

(10) Patent No.: US 8,303,559 B2
(45) Date of Patent: Nov. 6, 2012

(54) DISPOSABLE DIAPER

(75) Inventors: Hironao Minato, Kagawa (JP); Kaiyo Nakajima, Kagawa (JP); Naoko Takada, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 344 days.

(21) Appl. No.: 12/532,071

(22) PCT Filed: Feb. 18, 2008

(86) PCT No.: PCT/JP2008/052622
§ 371 (c)(1),
(2), (4) Date: Sep. 18, 2009

(87) PCT Pub. No.: WO2008/114556
PCT Pub. Date: Sep. 25, 2008

(65) Prior Publication Data
US 2010/0069871 A1    Mar. 18, 2010

(30) Foreign Application Priority Data

Mar. 19, 2007  (JP) ................................. 2007-069879
Jan. 17, 2008  (JP) ................................. 2008-008531

(51) Int. Cl.
*A61F 13/15*     (2006.01)
*A61F 13/20*     (2006.01)

(52) U.S. Cl. .......... 604/385.19; 604/385.23; 604/385.28

(58) Field of Classification Search ............. 604/385.19, 604/385.23, 385.28
See application file for complete search history.

(56) References Cited

U.S. PATENT DOCUMENTS

| | | | | |
|---|---|---|---|---|
| 5,342,342 | A * | 8/1994 | Kitaoka | 604/385.19 |
| 5,921,975 | A * | 7/1999 | Suzuki et al. | 604/385.17 |
| 6,152,907 | A * | 11/2000 | Widlund et al. | 604/385.08 |
| 6,383,170 | B1 * | 5/2002 | Mishima et al. | 604/385.19 |
| 6,616,644 | B1 * | 9/2003 | Mizutani | 604/385.04 |
| 6,786,895 | B1 * | 9/2004 | Schmitz | 604/385.28 |
| 2006/0135931 | A1 * | 6/2006 | Suzuki et al. | 604/385.19 |
| 2006/0142727 | A1 * | 6/2006 | Suzuki et al. | 604/385.19 |
| 2006/0173435 | A1 * | 8/2006 | Nakajima et al. | 604/385.19 |
| 2007/0078420 | A1 * | 4/2007 | Sugiyama et al. | 604/361 |
| 2007/0088302 | A1 * | 4/2007 | Sugiyama et al. | 604/378 |
| 2007/0088304 | A1 | 4/2007 | Sakano et al. | |

(Continued)

FOREIGN PATENT DOCUMENTS

EP     0 581 044 A2    2/1994
(Continued)

OTHER PUBLICATIONS

PCT/JP2008/052622 International Search Report, May 13, 2008.

*Primary Examiner* — Susan Su
(74) *Attorney, Agent, or Firm* — Lowe, Hauptman, Ham & Berner, LLP

(57) ABSTRACT

A disposable diaper is provided with a skin-contactable sheet piece above a liquid-pervious topsheet. The skin-contactable sheet piece is formed with openings extending in a back-and-forth direction through which body waste is guided toward the topsheet and both lateral zones of the sheet piece on both sides of these openings as viewed in a transverse direction are provided with elastic members attached under tension. Outside the skin-contactable sheet piece as viewed in the transverse direction, leak-barriers are provided and the lateral zones of the skin-contactable sheet piece are bonded to the leak-barriers along regions defined between proximal edges and free edges of the respective leak-barriers.

5 Claims, 7 Drawing Sheets

U.S. PATENT DOCUMENTS

2007/0088306 A1    4/2007  Sugiyama et al.
2007/0088310 A1*   4/2007  Sugiyama et al. ..... 604/385.101
2009/0005752 A1*   1/2009  Suzuki et al. ......... 604/385.101

FOREIGN PATENT DOCUMENTS

| | | |
|---|---|---|
| GB | 2 287 393 | 9/1995 |
| GB | 2 287 888 | 10/1995 |
| JP | 6-7725 U | 2/1994 |
| JP | 9-510384 | 10/1997 |
| JP | 9-510385 | 10/1997 |
| JP | 2002-011044 A | 1/2002 |
| JP | 2007-130435 | 5/2007 |
| JP | 2007-130442 | 5/2007 |
| JP | 2007-236911 | 9/2007 |
| WO | 95/25493 | 9/1995 |
| WO | 2007/091527 | 8/2007 |

* cited by examiner

DISPOSABLE DIAPER

RELATED APPLICATIONS

The present application is based on International Application PCT/JP2008/052622, filed Feb. 18, 2008, which claims priority from Japan Application No. 2007-69879, filed Mar. 19, 2007 and Japan Application No. 2008-8531, filed Jan. 17, 2008 the disclosures of which are hereby incorporated by reference herein in their entirety.

TECHNICAL FIELD

The present invention relates generally to a disposable diaper.

RELATED ART

In disposable diapers, various constructions intending to protect a diaper wearer's skin against possibly been soiled with body waste have already been proposed and known, for example, from PATENT DOCUMENT 1 and PATENT DOCUMENT 2.

The diaper disclosed in PATENT DOCUMENT 1 is of a pant-type and has a skin-contactable sheet above a liquid-pervious topsheet covering an absorbent assembly. This skin-contactable sheet has longitudinally opposite ends bonded to the top- or backsheets and is formed in a zone just above a crotch region of the diaper with an opening to guide feces therethrough to the crotch region. Surrounding the opening, an elastic member is attached under tension to the skin-contactable sheet so that the skin-contactable sheet would be spaced upward from the topsheet and come in contact with a wearer's skin as the diaper is put on the wearer's body.

The diaper disclosed in PATENT DOCUMENT 2 is of an open-type and has flexible flaps extending on both sides of a longitudinal axis of symmetry in the longitudinal direction. Each of these flaps is connected along one of its longitudinal side edges to an inner casing sheet and its zone laterally extending toward the longitudinal axis of symmetry is bonded to the other flap in the crotch region of the diaper except for the vicinity of anus in which these flaps are spaced from each other by 6 cm or less.
PATENT DOCUMENT 1: JP 2002-11044 A
PATENT DOCUMENT 2: JP 9-510385 T

DISCLOSURE OF THE INVENTION

Problem to be Solved by the Invention

While it is possible for the diaper disclosed in PATENT DOCUMENT 1 to prevent body waste such as feces from coming in contact with a wearer's skin, this diaper includes no positive means to prevent the body waste having passed through the opening and moving sideways on the topsheet from leaking out beyond the leg-openings. Consequentially, the wearer's leg skin might be soiled with body waste.

In the case of the diaper disclosed in PATENT DOCUMENT 2, each of the flexible flaps provided on both sides of the longitudinal axis of symmetry is connected along one of its side edges to the inner liquid-pervious casing sheet so as to prevent body waste laterally moving on this liquid-pervious casing sheet from leaking out beyond the leg-openings. However, the other side edge of the flap is connected to the associated side edge of the other flap in the crotch region and consequentially the flap might collapse onto the liquid-pervious casing sheet so as to form gaps between the flap and the wearer's leg rather than being raised up from the liquid-pervious sheet and kept in close contact with the wearer's leg. It may cause body waste to leak out through the gaps around the wearer's leg and to come in contact with the wearer's leg skin.

In view of the problems as have been described above, it is an object of the present invention to provide a disposable diaper allowing the problems of the conventional diapers to be effectively solved.

Measure to Solve the Problem

According to the present invention, there is provided a disposable diaper comprising: a crotch region having a back-and-forth direction and a transverse direction, a front waist region extending forward from the crotch region and a rear waist region extending rearward from the crotch region, a body fluid absorbent core being provided below a liquid-pervious sheet and above a liquid-impervious sheet, and skin-contactable sheet piece having opening allowing body waste to pass therethrough and extending in the back-and-forth direction being provided above the liquid-pervious sheet with opposite end zones of the skin-contactable sheet piece as viewed in the back-and-forth direction fixed to the front waist region and the rear waist region, respectively, so that a peripheral zone surrounding the opening is spaced upward from the liquid-pervious sheet to prevent the liquid-pervious sheet from coming in contact with a wearer's skin in the peripheral zone surrounding the opening.

The present invention further comprises: the opening of the skin-contactable sheet piece comprises a U-shaped front opening extending from the crotch region toward the front waist region and a U-shaped rear opening extending from the crotch region toward the rear waist region. The skin-contactable sheet piece comprising a pair of lateral zones extending in the back-and-forth direction on both sides of the openings as viewed in the transverse direction and an intermediate zone being provided between the front opening and the rear opening and connecting the lateral zones, wherein each of the lateral zones being provided with at least a single elastic member extending along the outer periphery of the opening in the back-and-forth direction and attached under tension to the skin-contactable sheet piece. The crotch region and the front and rear waist regions are further provided outside the skin-contactable sheet piece as viewed in the transverse direction with leak-barriers extending in the back-and-forth direction, wherein each of the leak-barriers comprises a fixed proximal edge extending in the back-and-forth direction, a deformable free edge extending in parallel to the fixed proximal edge and provided with an elastic member extending in the back-and-forth direction and attached under tension thereto and front and rear fixed ends opposed in the back-and-forth direction. Each of the lateral zones of the skin-contactable sheet piece is bonded to the associated leak-barrier in a region defined between the proximal edge and the free edge.

Effect of the Invention

In the case of the disposable diaper according to the present invention, the skin-contactable sheet piece is driven so as to be spaced from the liquid-pervious sheet in the crotch region because of the contraction of the elastic members attached to the lateral zones as the diaper is put on the wearer's body. In this state, the skin-contactable sheet piece having the respective lateral zones bonded to the respective leak-barriers assists the leak-barriers to be raised up. Since the opening of the skin-contactable sheet is U-shaped, an area of the skin-contactable sheet contacting with the wearer's skin can be reduced as much as possible. With this unique arrangement, the diaper according to the present invention can prevent the wearer from feeling stuffy. With the leak-barriers raised up in this manner, the free edges thereof easily come in contact with the wearer's legs and this enhances a preventive effect against leak of body waste beyond the leg-openings.

Figure 1:
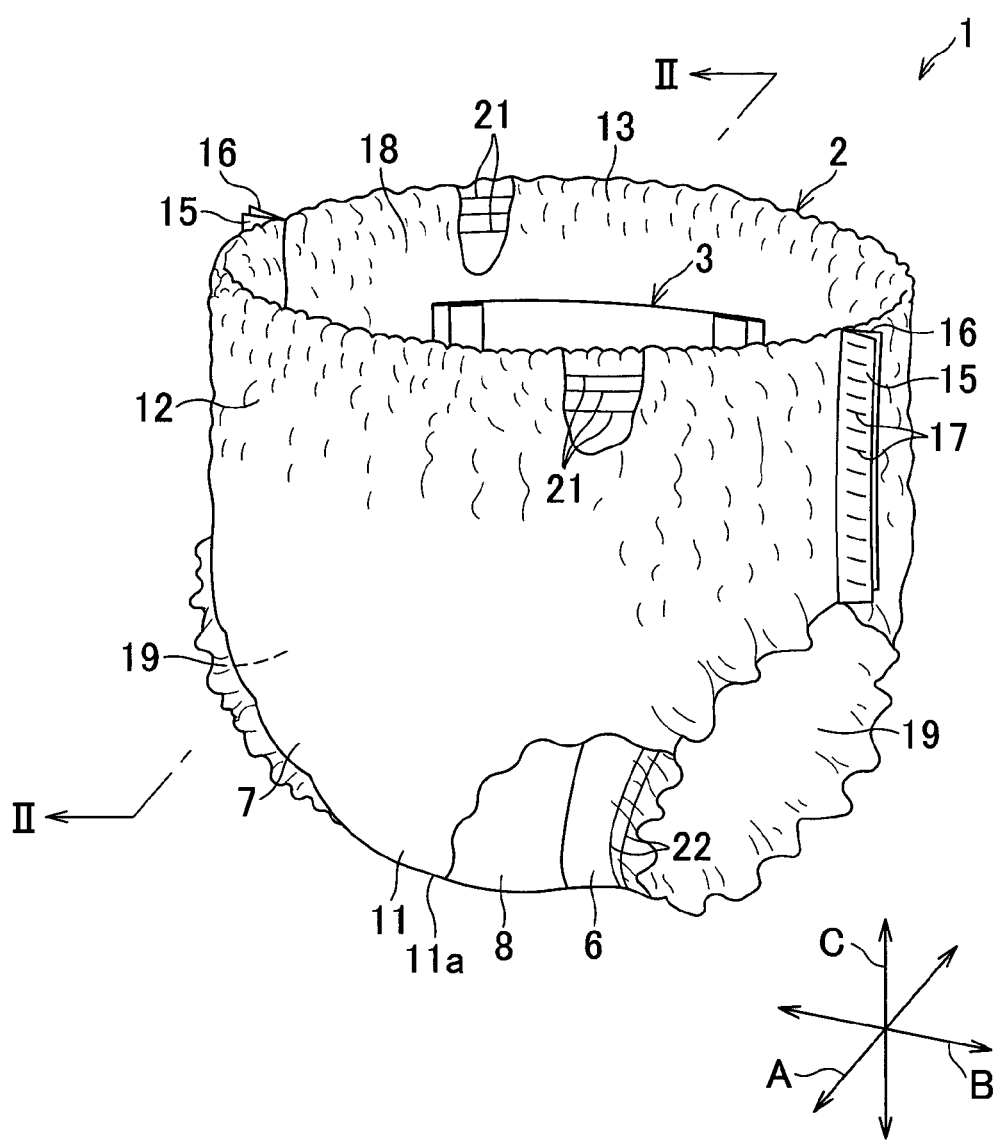
FIG. 1 is a partially cutaway perspective view of disposable diaper.

IDENTIFICATION OF REFERENCE NUMERALS USED IN THE DRAWINGS 1 disposable diaper
8 liquid-impervious sheet (leak-barrier sheet)
11 crotch region
12 front waist region
13 rear waist region
31 body fluid absorbent core
32 liquid-pervious sheet (topsheet)
33b skin-contactable sheet piece (skin-contactable sheet)
37, $37_L$, $37_R$ elastic member
38 front opening
39 rear opening
40, $40_L$, $40_R$ lateral zone
58, $58_L$, $58_R$ leak barrier
59a fixed proximal edge (bottom side)
59c free edge (top side)
59d front fixed end
59e rear fixed end
63, $63_L$, $63_R$ elastic member
A back-and-forth direction
B transverse direction

DETAILED DESCRIPTION OF THE PREFERRED EMBODIMENTS

Details of a disposable diaper according to the present invention will be more fully understood from the description given hereunder with reference to the accompanying drawings.

Figure 2:
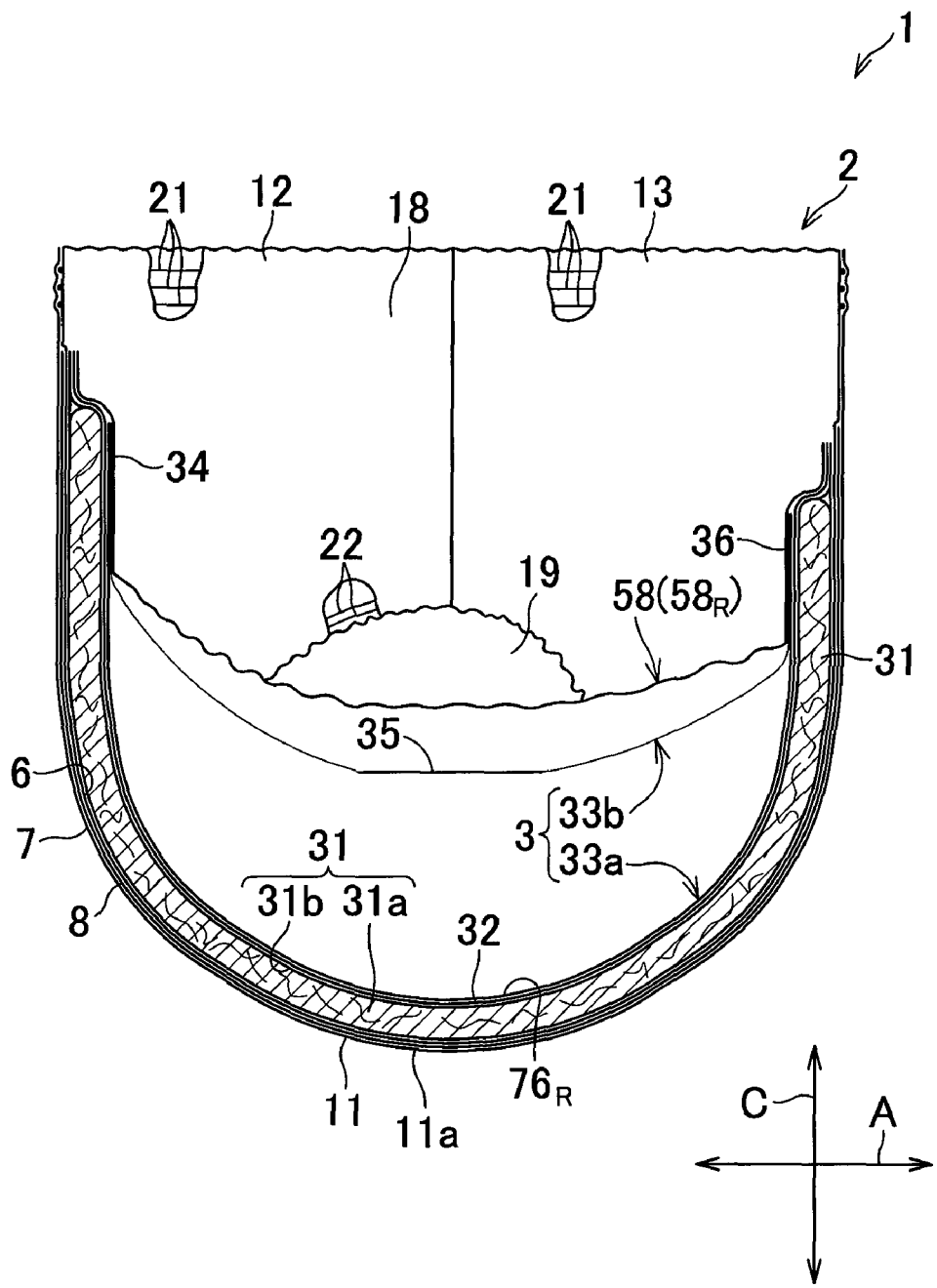
FIG. 2 is a sectional view taken along the line II-II in FIG. 1.

FIG. 1 is a partially cutaway perspective view of a diaper 1 and FIG. 2 is a sectional view taken along the line II-II in this perspective view. FIG. 1 shows the diaper 1 supposed to being on a wearer's body and indicates a back-and-forth direction, a transverse direction and a vertical direction by reference symbols A, B and C, respectively. The diaper 1 comprises a pant-type chassis 2 and a body fluid absorbent assembly 3 provided on the inner side of the chassis 2. The chassis 2 comprises an inner cover sheet 6, an outer cover sheet 7 and a liquid-impervious leak-barrier sheet 8 sandwiched between these two sheets 6, 7 so as to define a crotch region 11, a front waist region 12 extending forward from the crotch region 11 and a rear waist region 13 extending rearward from the crotch region 11. The front and rear waist regions 12, 13 are put flat together along respectively opposite side edges 15, 16 and bonded together at a plurality of spots 17 arranged along these side edges 15, 16 intermittently in the vertical direction C so as to form a waist-opening 18. Simultaneously, these front and rear waist regions 12, 13 cooperate with the crotch region 11 to form a pair of leg-openings 19. Along respective peripheries of the waist-opening 18 and the leg-openings 19, waist elastic members 21 and leg elastic members 22 are laid between the inner cover sheet 6 and the outer cover sheet 7 and bonded under tension to at least one of these sheets 6, 7. The body fluid absorbent assembly 3 is provided in the crotch region 11 to extend in the back-and-forth direction A and comprises a liquid-absorbent panel 33a and a skin-contactable sheet 33b. The liquid-absorbent panel 33a comprises, in turn, a body fluid absorbent core 31 formed by liquid-absorbent material 31a wrapped with tissue paper 31b and a liquid-pervious topsheet 32 adapted to cover at least a part of the surface of the core 31 facing the wearer's skin. The skin-contactable sheet 33b is provided above the topsheet 32, therefore being further close to the wearer's skin than the topsheet 32. As viewed in the back-and-forth direction A in FIG. 2, the skin-contactable sheet 33b has a front end zone 34 and a rear end zone 36 being permanently bonded to the topsheet 32 in the front and rear waist regions 12, 13, respectively, and an intermediate zone 35 spaced upward from the topsheet 32 in the crotch region 11. Referring to FIG. 2, the core 31 is below the topsheet 32 and above the leak-barrier sheet 8 so that the core 31 is covered with the leak-barrier sheet 8 from the outside of the diaper 1 and the body fluid absorbed by the core 31 is reliably prevented.

Figure 3:
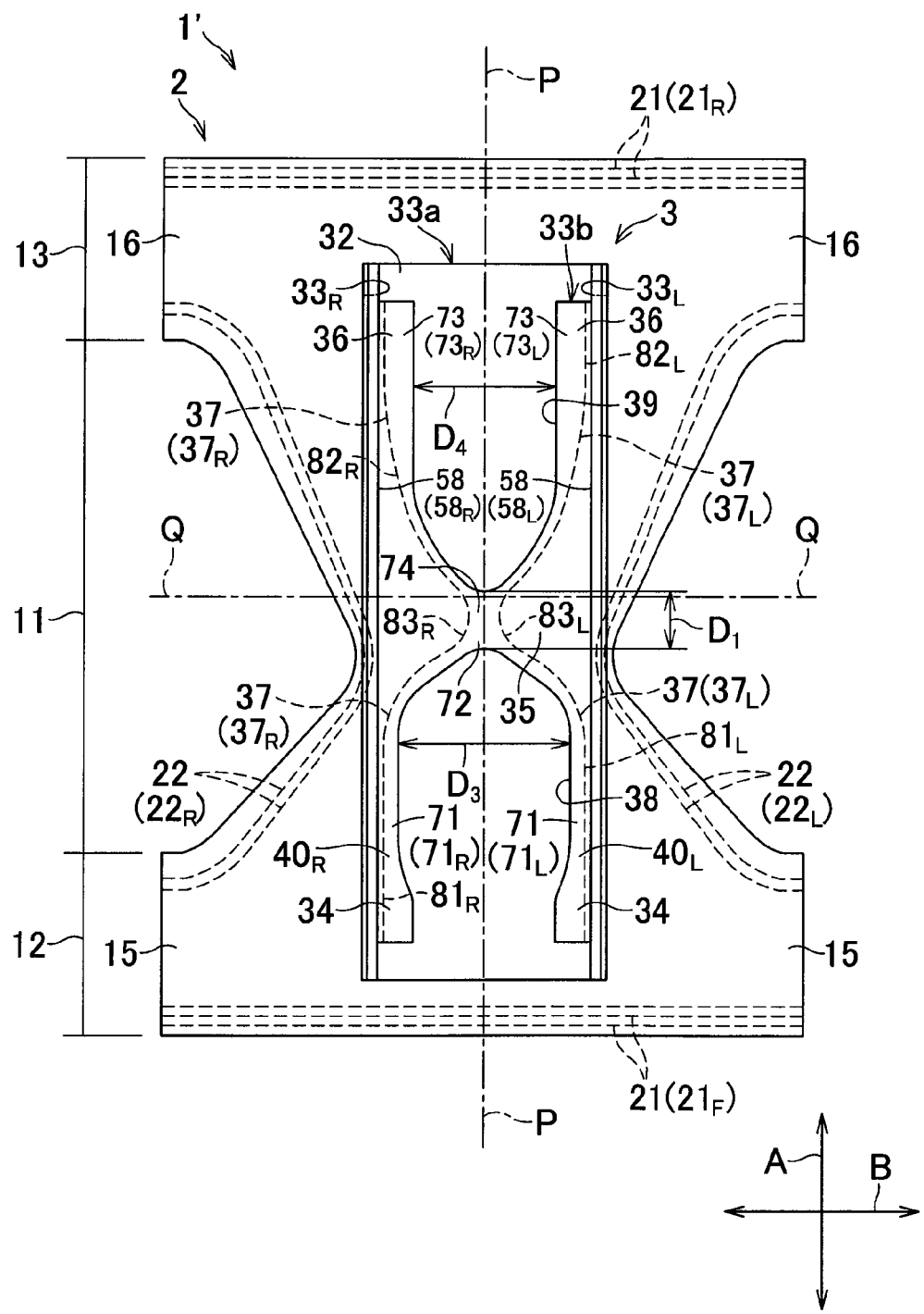
FIG. 3 is a plan view showing the diaper of FIG. 1 as developed and flattened.

FIG. 3 is a plan view of the diaper 1' corresponding to the diaper 1 of FIG. 1 having the front and rear waist regions 12, 13 peeled off from each other along respective arrays of the seal spots 17 and developed in the back-and-forth direction A as well as in the transverse direction B. Referring to FIG. 3, the diaper 1' is provided with front and rear waist elastic members $21_F$ and $21_R$ generically referred to as waist elastic member 21, left and right leg elastic members $22_L$, $22_R$ generically referred to as leg elastic members 22, and left and right crotch region elastic members $37_L$, $37_R$ generically referred to as crotch region elastic member 37 laid on the skin-contactable sheet 33b. These elastic members 21, 22 and 37 are attached under tension to the diaper 1' and indicated by dashed lines. Expression "left and right" used herein should be understood to be with respect to a wearer of the diaper 1. The diaper 1' has the longitudinal center line P-P bisecting a dimension in the transverse direction B and the transverse center line Q-Q in the back-and-forth direction A. The diaper 1' is symmetric about the longitudinal center line P-P. Referring to FIG. 3, the chassis 2 has a concave-shape curved inwardly and the body fluid absorbent assembly 3 is rectangular. The skin-contactable sheet 33b as one component of the body fluid absorbent assembly 3 is formed of a sheet piece made of a preferably liquid-impervious nonwoven fabric or a plastic film and comprises left and right lateral zones $40_L$, $40_R$ extending in the back-and-forth direction A along transversely opposite side edges $33_L$, $33_R$ of the liquid-absorbent panel 33a. These left and right lateral zones $40_L$, $40_R$ are connected with each other by the intermediary of an intermediate zone 35. The lateral zones $40_L$, $40_R$ cooperate with the intermediate zone 35 to define a U-shaped front opening 38 extending from the crotch region 11 toward the front waist region 12 and a U-shaped rear opening 39 extending from the crotch region 11 toward the rear waist region 13. The front opening 38 has left and right side edges $71_L$, $71_R$ generically referred to as side edges 71 and a bottom edge 72 by the intermediary of which the side edges $71_L$, $71_R$ are connected to each other. In the similar manner, the rear opening 39 has left and right side edges $73_L$, $73_R$ generically referred to as side edges 73 and a bottom edge 74 by the intermediary of which the side edges $73_L$, $73_R$ are connected to each other. Each of the crotch region elastic members $37_L$, $37_R$ associated with the skin-contactable sheet 33b preferably comprises a single rubber string and these respective rubber strings extend in the back-and-forth direction A along immediately outsides of the front opening 38 and the rear opening 39. With the crotch region 11 of the diaper 1 being curved in the back-and-forth direction A as seen in FIGS. 1 and 2, these elastic members $37_L$, $37_R$ contract in the back-and-forth direction A, resulting in that a dimension of the skin-contactable sheet 33b in the back-and-forth direction A is reduced and the intermediate zone 35 is spaced upward from the topsheet 32 (See FIG. 2).

The body fluid absorbent assembly 3 further includes a pair of leak-barriers $58_L$, $58_R$ generically referred to as leak-barrier 58 placed upon the side edges $40_L$, $40_R$ so as to extending in the back-to-forth direction A.

Figure 4:
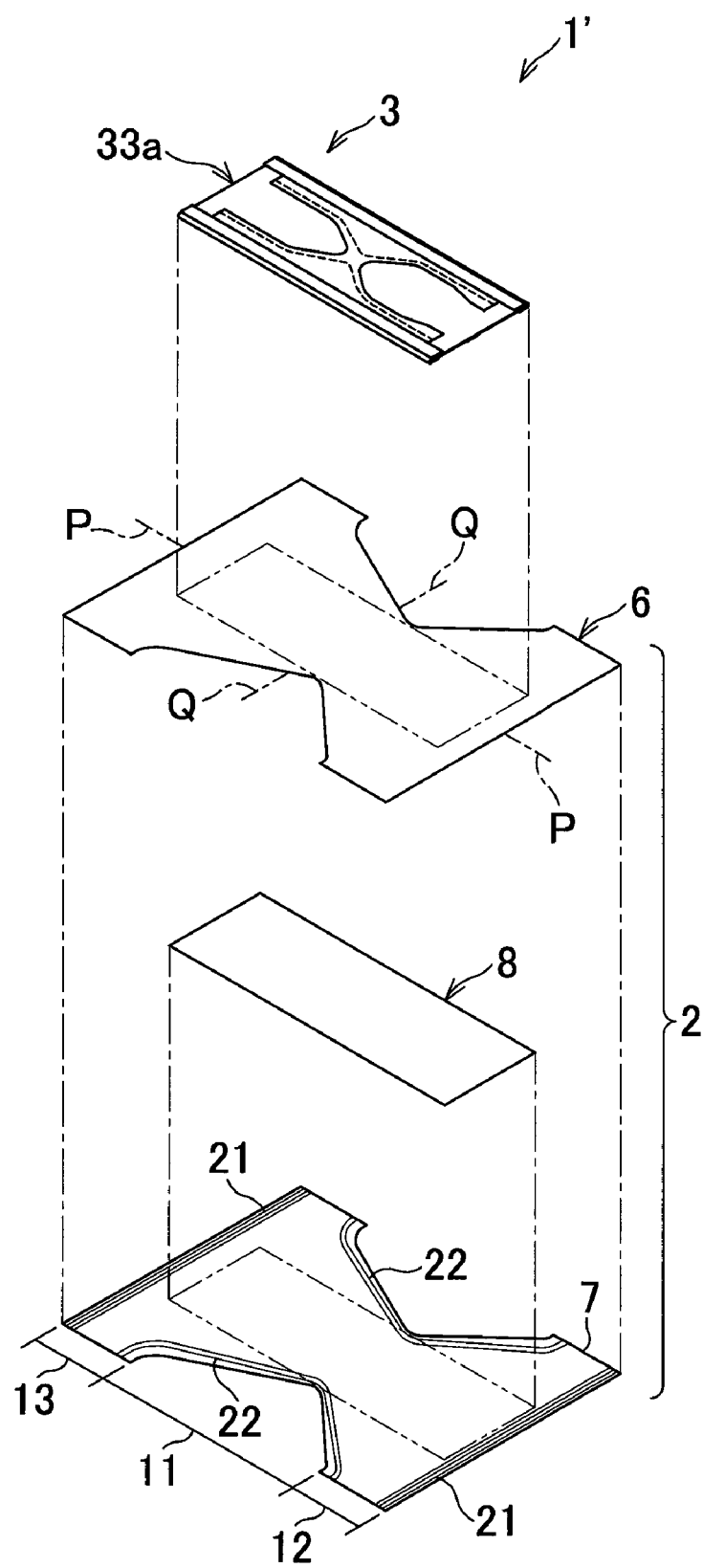
FIG. 4 is an exploded perspective view illustrating a manner in which the diaper of FIG. 3 is assembled.

FIG. 4 is an exploded view illustrating a manner in which the various components of the diaper 1' are assembled together. The outer cover sheet 7 is made of a nonwoven fabric or a plastic film and is provided on the inner surface (i.e., upper surface as viewed in FIG. 4) thereof with the waist elastic member 21 and the leg elastic member 22 attached under tension thereto by a hot melt adhesive (not shown). In addition to these elastic members 21, 22, the leak-barrier sheet 8 made of a liquid-impervious plastic film is bonded to the inner surface (i.e., upper surface as viewed in FIG. 4) by use of adhesive or welding technique. To the inner surface of these outer cover sheet 7 and leak-barrier sheet 8 bonded to each other in this manner, the inner cover sheet 6 made of a nonwoven fabric or a plastic film and being same as the outer cover sheet 7 in shape as well as size by use of adhesive or welding technique. To the inner surface (i.e., upper surface as viewed in FIG. 4) of the inner cover sheet 6, in turn, the outer surface (i.e., lower surface as viewed in FIG. 4) of the liquid-absorbent panel 33a as the one component of the body fluid absorbent assembly 3 is bonded over substantially entire area of the liquid absorbent panel 33a by a hot melt adhesive (not shown).

With the diaper 1 put on the wearer's body, it is desired to assure a proper condition that the wearer's external genital should be exposed in the front opening 38, the wearer's anus should be exposed in the rear opening 39 and the intermediate zone 35 should be in contact with the wearer's skin between the wearer's external genital and anus. To ensure such positional relationship, preferably, the bottom edge 72 of the front opening 38 is located forward from the transverse center line Q-Q and the bottom edge 74 of the rear opening 39 is co-aligned with or in the vicinity of the transverse center line Q-Q.

Dimensions of the respective components constituting the disposable diaper according to the invention not only depend on ages of its user, i.e., whether the diaper is for infants or for adults but also depend on the diaper's type, i.e., whether it is the diaper 1 of a pant-type as illustrated or of an open-type. In general, however, a dimension $D_1$ (See FIG. 3) of the intermediate zone 35 being co-aligned with the longitudinal center line P-P as measured in the back-and-forth direction A is preferably in a range of 20 to 70 mm. The respective maximum dimensions $D_3$, $D_4$ (See FIG. 3) of the front opening 38 and the rear opening 39 as measured in the transverse direction B are preferably in a range of 50 to 400 mm.

Figure 5:
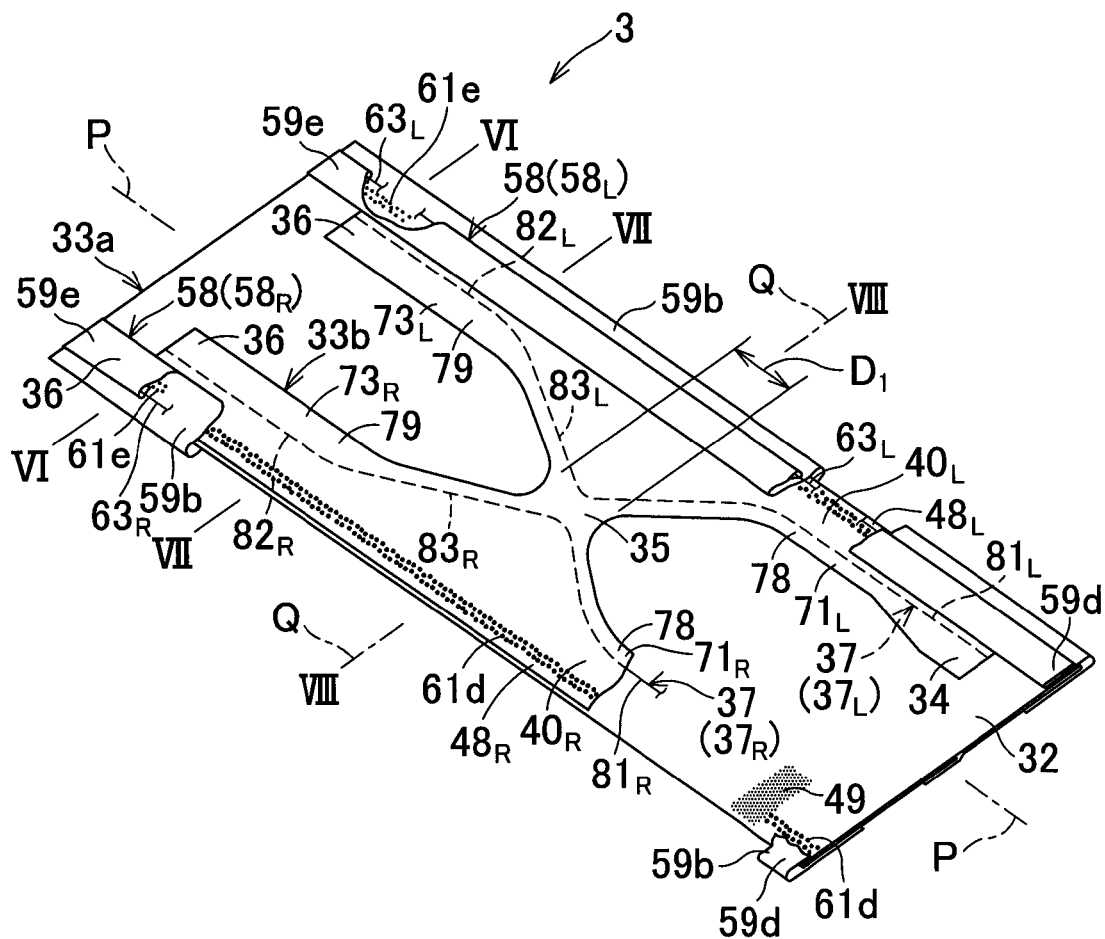
FIG. 5 is a scale-enlarged perspective view showing a body fluid absorbent assembly as partially broken away.
Figure 5:
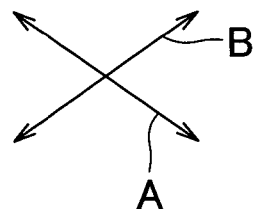
Figure 6:
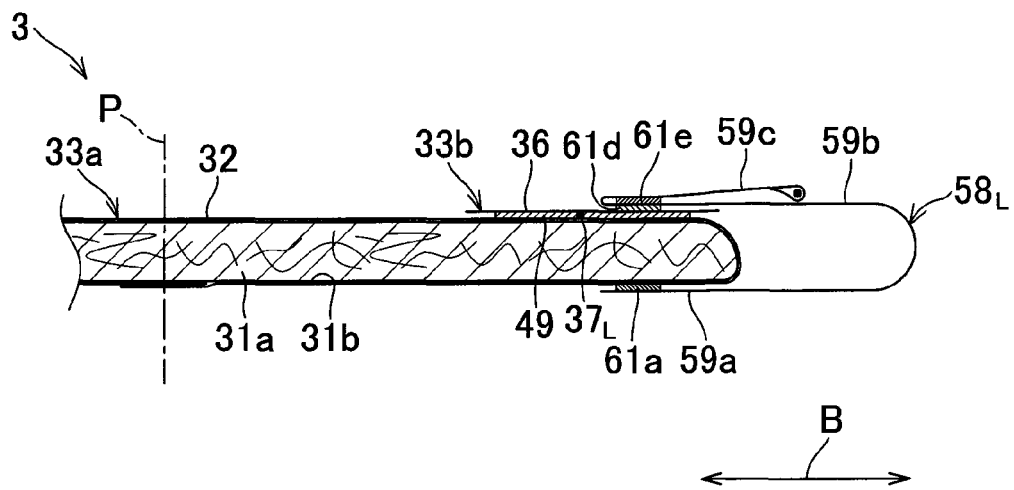
FIG. 6 is a sectional view taken along the line VI-VI in FIG. 5.
Figure 7:
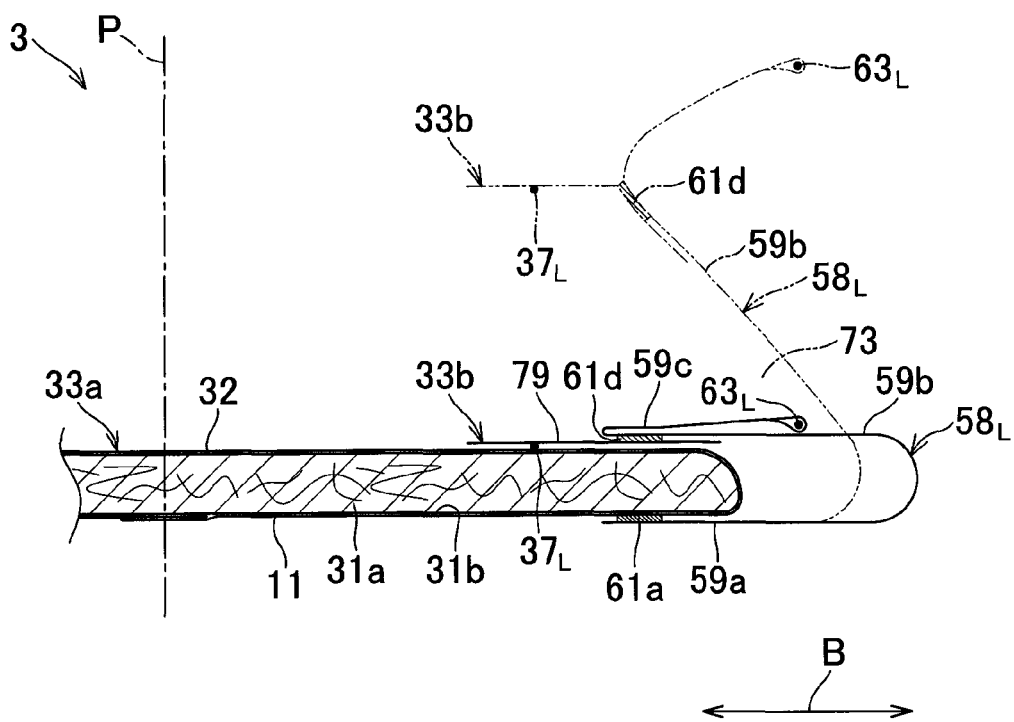
FIG. 7 is a sectional view taken along the line VII-VII in FIG. 5.
Figure 8:
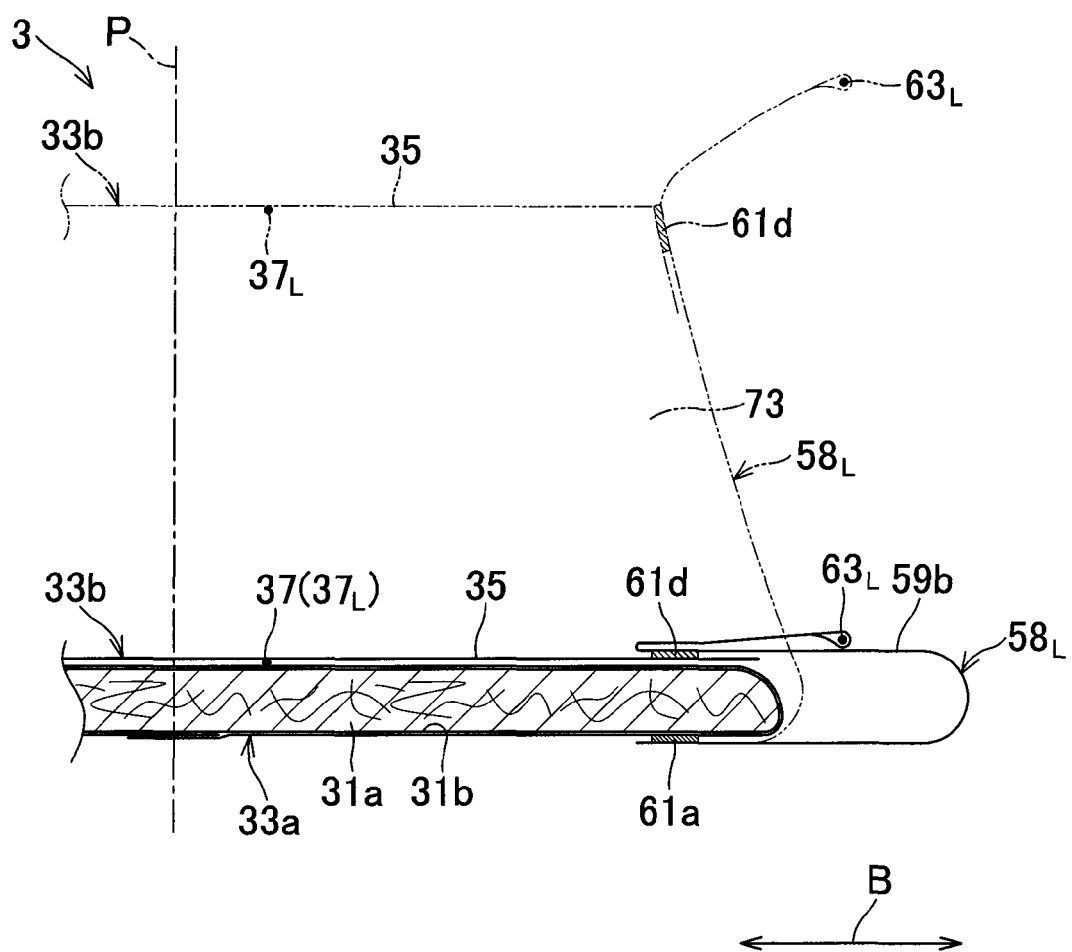
FIG. 8 is a sectional view taken along the line VIII-VIII in FIG. 5.

Of FIGS. 5 through 8 showing details of the body fluid absorbent assembly 3, FIG. 5 is a scale-enlarged perspective view showing the body fluid absorbent assembly 3 as partially broken away, FIG. 6 is a sectional view taken along the line VI-VI in FIG. 5, FIG. 7 is a sectional view taken along the line VII-VII in FIG. 5 and FIG. 8 is a sectional view taken along the line VIII-VIII in FIG. 5. It will be appreciated that the line VIII-VIII is co-aligned with the transverse center line Q-Q.

Referring to FIGS. 5 through 8, the liquid-absorbent panel 33a constituting the body fluid absorbent assembly 3 comprises the core 31 which comprises, in turn, the liquid-absorbent material 31a such as fluff pulp or a mixture of fluff pulp and super-absorbent polymer particles and wrapped with tissue paper 31b, and the topsheet 32. With respect to the liquid-absorbent panel 33a, the longitudinal center line P-P and the transverse center line Q-Q are indicated also in FIGS. 5 through 8. The skin-contactable sheet 33b made of a nonwoven fabric is provided on its lower surface as viewed in FIGS. 5 through 8 with the crotch region elastic members $37_L$, $37_R$ symmetrically about the longitudinal center line P-P and attached thereto under tension by a hot melt adhesive (not shown). The crotch region elastic member $37_L$ comprises first and second segments $81_L$, $82_L$ extending rather linearly along the side edges $71_L$, $73_L$ of the front opening 38 and the rear opening 39, respectively, and a third segment $83_L$ extending along the bottom edges 72, 74 of the intermediate zone 35 so as to become convex toward the longitudinal center line P-P. The other crotch region elastic member $37_R$ comprises first and second segments $81_R$, $82_R$ extending rather linearly along the side edges $71_R$, $73_R$ of the front opening 38 and the rear opening 39, respectively, and a third segment $83_R$ extending along the bottom edges 72, 74 of the intermediate zone 35 so as to become convex toward the longitudinal center line P-P. In the transverse direction B of the skin-contactable sheet 33b, the elastic members $37_L$, $37_R$ are closest to each other in the intermediate zone 35. The lateral zones $40_1$, $40_R$ of the skin-contactable sheet 33b comprise the front and rear end zones 34, 36 opposite to each other in the back-and-forth direction A and bonded to the topsheet 32 by a hot melt adhesive 49, the intermediate zone 35 connecting the lateral zones $40_L$, $40_R$ to each other and having a dimension $D_1$ (See FIG. 4) as measured in the back-and-forth direction A, a front zone 78 defined between the front end zone 34 and the intermediate zone 35, and a rear zone 79 defined between the rear end zone 36 and the intermediate zone 35.

Referring to FIG. 5, each of the leak-barriers $58_L$, $58_R$ provided on the body fluid absorbent assembly 3 comprises a sheet piece such as a nonwoven fabric or a plastic film folded in Z-shape or inverted Z-shape. These leak-barriers $58_L$, $58_R$ are preferably liquid-impervious. These leak-barriers $58_L$, $58_R$ respectively include elastic members $63_L$, $63_R$ generically referred to as elastic member 63 extending in the back-and-forth direction A and bonded thereto under tension. In FIGS. 6 through 8, the leak-barrier $58_L$ folded in inverted Z-shape is shown.

FIG. 6 illustrates a cross-section extending across the rear end zone 36 of the skin-contactable sheet 33b. As will be appreciated, a cross-section cut across the front end zone of the skin-contactable sheet 33b in parallel to the cross-section of FIG. 6 is substantially similar to the latter. Referring to FIG. 6, the rear end zone 36 has its substantially full width bonded to the topsheet 32 by a hot melt adhesive 49. The leak-barrier $58_L$ is provided outside the skin-contactable sheet 33b as viewed in the transverse direction B and, of the inverted Z-shape in which this leak-barrier $58_L$ is folded, a bottom side $59a$ is below the liquid-absorbent panel $33a$ and bonded thereto by a hot melt adhesive $61a$ and an intermediate side $59b$ is above the skin-contactable sheet $33b$ and bonded thereto by a hot melt adhesive $61d$. The intermediate side $59b$ and a top side $59c$ of the leak-barrier $58_L$ are bonded to each other by a hot melt adhesive $61e$. As will be apparent from FIG. 5, in the front and rear ends $59d$, $59e$ of the leak-barrier $58_L$ extending in the back-and-forth direction A beyond the skin-contactable sheet $33b$, the respective intermediate sides $59b$ is fixed to the topsheet 32 by a hot melt adhesive $61d$.

FIG. 7 illustrates a cross-section extending across the rear zone 79 of the skin-contactable sheet $33b$. It will be appreciated that a cross-section extending across the front zone 78 of the skin-contactable sheet $33b$ in parallel to the line VII-VII is substantially similar to FIG. 7. Referring to FIG. 7, the rear zone 79 of the skin-contactable sheet $33b$ is not bonded to the topsheet 32 and consequently free to be spaced from the topsheet 32. In the leak-barrier $58_L$, the bottom side $59a$ is partially bonded to the liquid-absorbent panel $33a$ by a hot melt adhesive $61a$ so as to extend in the back-and-forth direction A and thereby to define a proximal edge while the top side $59c$ is provided with the elastic member $63_L$ attached thereto under tension so as to define a free edge extending in parallel to the proximal edge and being elastically deformable. The skin-contactable sheet $33b$ is bonded to the leak-barrier 58 along an intermediate zone defined between these proximal edge and the free edge. When the diaper 1 having the body fluid absorbent assembly 3 of FIG. 5 is put on the wearer's body as shown in FIG. 1, the elastic members $37_L$, $63_L$ contract and the skin-contactable sheet $33b$ and the leak-barrier $58_L$ associated with these elastic members $37_L$, $63_L$ take positions indicated by imaginary lines in FIG. 7. Specifically, the skin-contactable sheet $33b$ is spaced upward from the topsheet 32 and the skin-contactable sheet $33b$ pulls up the intermediate side $59b$ of the leak-barrier $58_L$ so as to rise up. Such leak-barrier $58_L$ is adapted to be smoothly raised up as the diaper 1 is put on the wearer's body. On the other hand, the skin-contactable sheet $33b$ restrains movement of the intermediate side $59b$ in the transverse direction B and thereby prevents the leak-barrier $58_L$ from collapsing outward, i.e., rightward as viewed in FIG. 7 with respect to the crotch region 11. Consequentially, it is ensured for the diaper 1 to form, between the topsheet 32 and the leak-barrier $58_L$, a pocket 73 adapted to receive body fluid flowing in the transverse direction B. This pocket 73 opens inward as viewed in the transverse direction B. Furthermore, the skin-contactable sheet $33b$ is reliably kept in contact with the wearer's skin and thereby prevents body waste present on the topsheet 32 from soiling the wearer's skin around the front opening 38 and the rear opening 39.

When the diaper 1 is put on, it is raised up along the wearer's body until the intermediate zone 35 of the skin-contactable sheet $33b$ meets with the wearer's crotch. In this position of the diaper 1, the liquid-absorbent panel $33a$ is below the intermediate zone 35 and a space 80 is formed between the liquid-absorbent panel $33a$ and the intermediate zone 35. Even though the wearer raises the diaper 1 up too tightly, the moving of the diaper 1 would stop when the intermediate zone 35 meets with the wearer's crotch, therefore the space 80 would not be lost because of such a way to wear. The space 80 can surely be formed and prevent body wastes from contacting with the wearer's skin. Such skin-contactable sheet $33b$ has a shape as shown in FIG. 3. When the front and rear waist elastic members $21_F$ and $21_R$ contract and a dimension of the diaper 1 as viewed in the transverse direction B is seemingly getting smaller, the skin-contactable sheet $33b$ would get wrinkles a little in the intermediate zone 35. However, the skin-contactable sheet $33b$ would not get wrinkles too much to be fit with the wearer's skin. Furthermore, an area of the skin-contactable sheet contacting with the wearer's skin can be reduced as much as possible to prevent the wearer from feeling stuffy.

FIG. 8 illustrates a cross-section extending across the intermediate zone 35 of the skin-contactable sheet $33b$. The manner in which the skin-contactable sheet $33b$ and the leak-barrier $58_L$ are bonded together is similar to the manner having been described in reference with FIG. 7, i.e., the skin-contactable sheet $33b$ is bonded to the intermediate side $59b$ of the leak-barrier $58_L$ by a hot melt adhesive $61d$ and the leak-barrier $58_L$ is, in turn, above the outer surface of the liquid-absorbent panel $33a$ and bonded thereto by a hot melt adhesive $61a$. When the diaper 1 is put on the wearer's body as illustrated in FIG. 1, the skin-contactable sheet $33b$ and the leak-barrier $58_L$ in FIG. 8 takes positions as indicated by imaginary lines and the pocket 73 is formed. This pocket 73 is continuous with the pocket 73 of FIG. 7 as viewed in the back-and-forth direction A. The intermediate zone 35 of the skin-contactable sheet $33b$ extends across the liquid-absorbent panel $33a$ and, at the positions indicated by the imaginary lines, reliably comes in contact with the wearer's skin defined between the external genital and the anus of the wearer so that the liquid-absorbent panel $33a$ having absorbed body waste therein can be reliably prevented from coming in contact with the wearer's skin. As will be apparent from FIG. 8, the skin-contactable sheet $33b$ serves also in its intermediate zone to facilitate the leak-barrier $58_L$ to rise up and to prevent the leak-barrier $58_L$ from collapsing outward with respect to the crotch region 11. Such operative relationship between the skin-contactable sheet $33b$ and the leak-barrier $58_L$ assists also the skin-contactable sheet $33b$ to be spaced upward from the topsheet 32 as the leak-barrier $58_L$ is raised upward under contraction of the elastic member $63_L$ attached thereto.

The invention claimed is:
1. A disposable diaper comprising:
  a crotch region having a back-and-forth direction and a transverse direction perpendicular to the back-and-forth direction;
  a front waist region extending forward from said crotch region in the back-and-forth direction;
  a rear waist region extending rearward from said crotch region in the back-and-forth direction;
  a body fluid absorbent core sandwiched between a liquid-pervious sheet and a liquid-impervious sheet in said crotch region in a thickness direction of the crotch region;
  a skin-contactable sheet piece arranged above said liquid-pervious sheet and extending in said back-and-forth direction, wherein said skin-contactable sheet piece includes an opening allowing body waste to pass therethrough and opposite front and rear end zones as viewed in said back-and-forth direction fixed to said front waist region and said rear waist region, respectively, so that a peripheral zone of the skin-contactable sheet piece surrounding said opening is spaced upward from said liquid-pervious sheet to prevent said liquid-pervious sheet from coming in contact with a wearer's skin in said peripheral zone surrounding said opening,
  wherein
  said opening of said skin-contactable sheet piece includes a U-shaped front opening extending from said crotch region toward said front waist region and a U-shaped rear opening extending from said crotch region toward said rear waist region;
said skin-contactable sheet piece further includes
a pair of lateral zones extending in said back-and-forth direction on both sides of said openings as viewed in said transverse direction,
an intermediate zone between said front opening and said rear opening and connecting said lateral zones, and
a pair of elastic members attached under tension to said skin-contactable sheet piece and extending along outer peripheries of said openings in the back-and-forth direction without intersecting each other;
said disposable diaper further comprises transversely opposite leak-barriers attached to said skin-contactable sheet piece and extending in said back-and-forth direction,
each of said leak-barriers includes
a fixed proximal edge extending in said back-and-forth direction,
an elastically deformable free edge extending along said fixed proximal edge and including an elastic member extending in said back-and-forth direction and attached under tension thereto and
front and rear fixed ends opposed in said back-and-forth direction, and
each of said lateral zones of said skin-contactable sheet piece is directly bonded to associated said leak-barrier in a bonding region defined between said proximal edge and said free edge,
said skin-contactable sheet piece is directly bonded to the liquid-pervious sheet at the front and rear end zones in the bonding region defined between said proximal edge and said free edge, and
said skin-contactable sheet piece is not directly bonded to the liquid-pervious sheet between the front and rear end zones in the lateral zones so as to form a pocket between the liquid-pervious sheet and the skin-contactable sheet piece and between the front end zone and the rear end zone for receiving body waste.

2. A disposable diaper comprising:
a crotch region having a back-and-forth direction and a transverse direction perpendicular to the back-and-forth direction;
a front waist region extending forward from said crotch region in the back-and-forth direction;
a rear waist region extending rearward from said crotch region in the back-and-forth direction;
a body fluid absorbent core sandwiched between a liquid-pervious sheet and a liquid-impervious sheet in said crotch region in a thickness direction of the crotch region;
a skin-contactable sheet piece arranged above said liquid-pervious sheet and extending in said back-and-forth direction, wherein said skin-contactable sheet piece includes an opening allowing body waste to pass therethrough and opposite front and rear end zones as viewed in said back-and-forth direction fixed to said front waist region and said rear waist region, respectively, so that a peripheral zone of the skin-contactable sheet piece surrounding said opening is spaced upward from said liquid-pervious sheet to prevent said liquid-pervious sheet from coming in contact with a wearer's skin in said peripheral zone surrounding said opening,
wherein said opening of said skin-contactable sheet piece includes a U-shaped front opening extending from said crotch region toward said front waist region and a U-shaped rear opening extending from said crotch region toward said rear waist region;
said skin-contactable sheet piece further includes
a pair of lateral zones extending in said back-and-forth direction on both sides of said openings as viewed in said transverse direction,
an intermediate zone between said front opening and said rear opening and connecting said lateral zones, and
a pair of elastic members attached under tension to said skin-contactable sheet piece and extending along outer peripheries of said openings in the back-and-forth direction without intersecting each other;
said disposable diaper further comprises transversely opposite leak-barriers attached to said skin-contactable sheet piece and extending in said back-and-forth direction,
each of said leak-barriers includes
a fixed proximal edge extending in said back-and-forth direction,
an elastically deformable free edge extending along said fixed proximal edge and including an elastic member extending in said back-and-forth direction and attached under tension thereto and
front and rear fixed ends opposed in said back-and-forth direction, and
each of said lateral zones of said skin-contactable sheet piece is directly bonded to associated said leak-barrier in a bonding region defined between said proximal edge and said free edge,
the rear end zone has a substantially entire width in the transverse direction directly bonded to the liquid-pervious sheet.

3. A disposable diaper comprising:
a crotch region having a back-and-forth direction and a transverse direction perpendicular to the back-and-forth direction;
a front waist region extending forward from said crotch region in the back-and-forth direction;
a rear waist region extending rearward from said crotch region in the back-and-forth direction;
a body fluid absorbent core sandwiched between a liquid-pervious sheet and a liquid-impervious sheet in said crotch region in a thickness direction of the crotch region;
a skin-contactable sheet piece arranged above said liquid-pervious sheet and extending in said back-and-forth direction, wherein said skin-contactable sheet piece includes an opening allowing body waste to pass therethrough and opposite front and rear end zones as viewed in said back-and-forth direction fixed to said front waist region and said rear waist region, respectively, so that a peripheral zone of the skin-contactable sheet piece surrounding said opening is spaced upward from said liquid-pervious sheet to prevent said liquid-pervious sheet from coming in contact with a wearer's skin in said peripheral zone surrounding said opening,
wherein said opening of said skin-contactable sheet piece includes a U-shaped front opening extending from said crotch region toward said front waist region and a U-shaped rear opening extending from said crotch region toward said rear waist region;
said skin-contactable sheet piece further includes
a pair of lateral zones extending in said back-and-forth direction on both sides of said openings as viewed in said transverse direction, an intermediate zone between said front opening and said rear opening and connecting said lateral zones, and a pair of elastic members attached under tension to said skin-contactable sheet piece and extending along outer peripheries of said openings in the back-and-forth direction without intersecting each other;

said disposable diaper further comprises transversely opposite leak-barriers attached to said skin-contactable sheet piece and extending in said back-and-forth direction, each of said leak-barriers includes
a fixed proximal edge extending in said back-and-forth direction,
an elastically deformable free edge extending along said fixed proximal edge and including an elastic member extending in said back-and-forth direction and attached under tension thereto and
front and rear fixed ends opposed in said back-and-forth direction, and each of said lateral zones of said skin-contactable sheet piece is directly bonded to associated said leak-barrier in a first bonding region defined between said proximal edge and said free edge, said leak-barriers are each folded in an inverted Z-shape, and each of said leak-barriers further comprises
a top side arranged above the skin-contactable sheet piece and extending outwardly in the transverse direction,
a bottom side arranged below the skin-contactable sheet piece in the thickness direction, and
an intermediate side connecting the top side and the bottom side, said top side is directly bonded to the intermediate side in a second bonding region, said intermediate side is directly bonded to the skin-contactable sheet piece in the first bonding region, said skin-contactable sheet piece is directly bonded to the liquid-pervious sheet in a third bonding region defined between the fixed proximal edge and the elastically deformable free edge, and the first, second, and third bonding regions overlap each other in the thickness direction.

4. The disposable diaper according to claim 3, wherein a dimension of the third bonding region in the transverse direction is greater than that of the first bonding region in the transverse direction and than that of the second bonding region in the transverse direction.

5. A disposable diaper comprising:
a crotch region having a back-and-forth direction and a transverse direction perpendicular to the back-and-forth direction;
a front waist region extending forward from said crotch region in the back-and-forth direction;
a rear waist region extending rearward from said crotch region in the back-and-forth direction;
a body fluid absorbent core sandwiched between a liquid-pervious sheet and a liquid-impervious sheet in said crotch region in a thickness direction of the crotch region;
a skin-contactable sheet piece arranged above said liquid-pervious sheet and extending in said back-and-forth direction, wherein said skin-contactable sheet piece includes an opening allowing body waste to pass therethrough and opposite front and rear end zones as viewed in said back-and-forth direction fixed to said front waist region and said rear waist region, respectively, so that a peripheral zone of the skin-contactable sheet piece surrounding said opening is spaced upward from said liquid-pervious sheet to prevent said liquid-pervious sheet from coming in contact with a wearer's skin in said peripheral zone surrounding said opening,
wherein said opening of said skin-contactable sheet piece includes a U-shaped front opening extending from said crotch region toward said front waist region and a U-shaped rear opening extending from said crotch region toward said rear waist region;
said skin-contactable sheet piece further includes
a pair of lateral zones extending in said back-and-forth direction on both sides of said openings as viewed in said transverse direction,
an intermediate zone between said front opening and said rear opening and connecting said lateral zones, and
a pair of elastic members attached under tension to said skin-contactable sheet piece and extending along outer peripheries of said openings in the back-and-forth direction without intersecting each other;
said disposable diaper further comprises transversely opposite leak-barriers attached to said skin-contactable sheet piece and extending in said back-and-forth direction,
each of said leak-barriers includes
a fixed proximal edge extending in said back-and-forth direction,
an elastically deformable free edge extending along said fixed proximal edge and including an elastic member extending in said back-and-forth direction and attached under tension thereto and
front and rear fixed ends opposed in said back-and-forth direction, and
each of said lateral zones of said skin-contactable sheet piece is directly bonded to associated said leak-barrier in a bonding region defined between said proximal edge and said free edge,
the skin-contactable sheet piece is directly bonded to (i) the leak-barriers at the front end zone in the bonding region defined between the fixed proximal edge and the elastically deformable free edge and (ii) the liquid-pervious sheet at the front end zone.

* * * * *